(12) United States Patent
Allen et al.

(10) Patent No.: US 9,330,820 B2
(45) Date of Patent: May 3, 2016

(54) METHOD FOR MAKING ELECTRICALLY CONDUCTIVE THREE-DIMENSIONAL STRUCTURES

(71) Applicants: Mark G. Allen, Atlanta, GA (US); Seong-O Choi, Atlanta, GA (US); Jung-Hwan Pauk, Atlanta, GA (US); Xiaosong Wu, Atlanta, GA (US); Yanzhu Zhao, Atlanta, GA (US); Yong-Kyu Yoon, Smyma, GA (US); Swaminathan Rajaraman, Atlanta, GA (US)

(72) Inventors: Mark G. Allen, Atlanta, GA (US); Seong-O Choi, Atlanta, GA (US); Jung-Hwan Pauk, Atlanta, GA (US); Xiaosong Wu, Atlanta, GA (US); Yanzhu Zhao, Atlanta, GA (US); Yong-Kyu Yoon, Smyma, GA (US); Swaminathan Rajaraman, Atlanta, GA (US)

(73) Assignee: GEORGIA TECH RESEARCH CORPORATION, Atlanta, GA (US)

( * ) Notice: Subject to any disclaimer, the term of this patent is extended or adjusted under 35 U.S.C. 154(b) by 421 days.

(21) Appl. No.: 13/873,961

(22) Filed: Apr. 30, 2013

(65) Prior Publication Data
US 2013/0306356 A1    Nov. 21, 2013

Related U.S. Application Data

(62) Division of application No. 11/754,680, filed on May 29, 2007, now abandoned.

(60) Provisional application No. 60/809,049, filed on May 26, 2006.

(51) Int. Cl.
H01B 13/00    (2006.01)
A61B 5/00     (2006.01)
(Continued)

(52) U.S. Cl.
CPC .............. *H01B 13/00* (2013.01); *A61B 5/685* (2013.01); *A61M 37/0015* (2013.01);
(Continued)

(58) Field of Classification Search
CPC ........ C25D 1/003; C25D 1/10; C23C 14/005; C23C 14/04–14/048; C23C 16/01; C23C 16/04–16/047; C23C 18/1603–18/1616
USPC ......................................................... 205/136
See application file for complete search history.

(56) References Cited

U.S. PATENT DOCUMENTS 5,525,205 A * 6/1996 Miyashita ..................... 205/126
6,334,856 B1   1/2002 Allen et al.
(Continued)

FOREIGN PATENT DOCUMENTS

WO        03024507      3/2003
WO      2006138719     12/2006

OTHER PUBLICATIONS

Armani, D.K.; Chang Liu, "Microfabrication technology for polycaprolactone, a biodegradable polymer," Micro Electro Mechanical Systems, 2000. MEMS 2000. The Thirteenth Annual International Conference on , vol., no., pp. 294,299, Jan. 23-27, 2000.*

(Continued)

*Primary Examiner* — Luan Van
*Assistant Examiner* — Louis Rufo
(74) *Attorney, Agent, or Firm* — Troutman Sanders LLP; Ryan A. Schneider; Benjamin C. Wiles

(57) ABSTRACT

Methods are provided for fabricating three-dimensional electrically conductive structures. Three-dimensional electrically conductive microstructures are also provided. The method may include providing a mold having at least one microdepression which defines a three-dimensional structure; filling the microdepression of the mold with at least one substrate material; molding the at least one substrate material to form a substrate; and depositing and patterning of at least one electrically conductive layer either during the molding process or subsequent to the molding process to form an electrically conductive structure. In one embodiment, the three-dimensional electrically conductive microstructure comprises an electrically functional microneedle array comprising two or more microneedles, each including a high aspect ratio, polymeric three dimensional substrate structure which is at least substantially coated by an electrically conductive layer.

31 Claims, 8 Drawing Sheets

(51) Int. Cl.
  *A61M 37/00* (2006.01)
  *H05K 1/02* (2006.01)
  *C25D 1/00* (2006.01)
  *C25D 1/10* (2006.01)
  *C25D 5/02* (2006.01)
  *A61N 1/32* (2006.01)
  *H05K 3/40* (2006.01)
  *H05K 3/20* (2006.01)

(52) U.S. Cl.
  CPC ............... *C25D 1/003* (2013.01); *C25D 1/10* (2013.01); *C25D 5/022* (2013.01); *H05K 1/02* (2013.01); *H05K 3/4007* (2013.01); *A61B 2562/125* (2013.01); *A61M 2037/0053* (2013.01); *A61N 1/327* (2013.01); *H05K 3/20* (2013.01); *H05K 2201/0367* (2013.01); *H05K 2201/09045* (2013.01); *H05K 2201/09118* (2013.01); *H05K 2203/0113* (2013.01); *Y10T 428/298* (2015.01); *Y10T 428/2958* (2015.01)

(56) References Cited

U.S. PATENT DOCUMENTS

| | | | |
|---|---|---|---|
| 6,713,291 | B2 | 3/2004 | King et al. |
| 6,881,318 | B2 | 4/2005 | Hey et al. |
| 7,196,666 | B2 | 3/2007 | Allen et al. |
| 7,226,439 | B2 | 6/2007 | Prausnitz et al. |
| 2002/0133129 | A1* | 9/2002 | Arias et al. ............ 604/272 |
| 2002/0138049 | A1 | 9/2002 | Allen et al. |
| 2002/0142587 | A1 | 10/2002 | Allen et al. |
| 2003/0135166 | A1* | 7/2003 | Gonnelli ............ 604/264 |
| 2004/0164839 | A1 | 8/2004 | Park et al. |
| 2004/0203124 | A1 | 10/2004 | King et al. |
| 2006/0017650 | A1 | 1/2006 | Allen et al. |
| 2007/0276318 | A1 | 11/2007 | Henley |
| 2008/0063866 | A1 | 3/2008 | Allen et al. |
| 2080/0312610 | | 12/2008 | Binks et al. |

OTHER PUBLICATIONS

Hur, Seung-Hyun and Khang, Dahl-Young and Kocabas, Coskun and Rogers, John A., "Nanotransfer printing by use of noncovalent surface forces: Applications to thin-film transistors that use single-walled carbon nanotube networks and semiconducting polymers" Applied Physics Letters, 85, 5730-5732 (2004).*

Jung-Hwan Park, Mark G. Allen, Mark R. Prausnitz, Biodegradable polymer microneedles: Fabrication, mechanics and transdermal drug delivery, Journal of Controlled Release, vol. 104, Issue 1, May 5, 2005, pp. 51-66.*

Choi, Seong-O et al., "An Electrically Active Microneedle Array for Electroporation of Skin for Gene Delivery," Controlled Release Society 32nd Annual Meeting & Exposition, 2005.

Choi, Seong-O et al., "An Electrically Active Microneedle Array for Electroporation of Skin for Gene Delivery," Tech. Dig. 13th Int. Conf. Solid-State Sensors, Actuators, and Microsystems, Transducers 05, 2005.

Choi, Seong-O et al., "3-D Palterned Microstructures Using Inclined UV Exposure and Metal Transfer Micromolding," Tech Dig Solid-State Sensor. Actuator, and Microsystems Workshop, Hilton Head, 2006.

Han, Manhee et al., "3-D Microfabrication Using Inclined/Rotated UV Lithography," Sensors and Actuators A, vol. III, pp. 14-20, Mar. 1, 2004.

Hooper, Jay W. et al., "Smallpox DNA Vaccine Delivered by Novel Skin Electroporation Device Protects Mice Against Intransal Poxvirus Challenge," Vaccine 25, pp. 1814-1823, 2007.

Sato, Hironobu et al., "In-Channel Micromesh Structures Using Maskless Multi-Angle Exposure and their Microfilter Application," Sensors and Actuators A, vol. III, pp. 87-92, 2004.

Talbot, Neil H. et al., "Polymolding: Two Wafer Polysilicon Micromolding of Closed-Flow Passages for Microneedles and Microfluidic Devices," Proceedings of the Solid State Sensor and Actuator Workshop, pp. 265-268, Jun. 8-11, 1998.

Yoon, Yong-Kyu et al., "Multidirectional UV Lithography for Complex 3-D MEMS Structures," IEEE, Journal of Microelectromechanical Systems, vol. 15, No. 5, Oct. 2006.

Yoon, Yong-Kyu et al., "Integrated Vertical Screen Microfilter System using Inclined SU-8 Structures," Proceedings of IEEE MEMS Conf., pp. 227-230, 2003.

* cited by examiner

Inclined UV exposure

Rigid mold

Mold master

Flexible mold

Final structure

METHOD FOR MAKING ELECTRICALLY CONDUCTIVE THREE-DIMENSIONAL STRUCTURES

CROSS-REFERENCE TO RELATED APPLICATIONS

This application claims the benefit of U.S. patent application Ser. No. 11/754,680, filed May 29, 2007, which claims priority to U.S. Provisional Application No. 60/809,049, filed May 26, 2006. Both applications are hereby incorporated by reference herein.

FIELD OF THE INVENTION

The present invention relates generally to methods for making electrically functional three-dimensional structures, including high-aspect ratio structures, and more particularly to microscale structures made by applying and patterning electrically conductive layers onto substrates.

BACKGROUND OF THE INVENTION

Electrically functional three-dimensional structures have a variety of uses in biomedical, chemical, physical, and electronic applications. Non-limiting examples of these applications include electrically active microneedle arrays for transdermal gene therapy or drug delivery by electroporation, high-aspect-ratio metal pillar arrays for solid fuel combustion, and electromagnetically radiating antenna arrays, among other uses.

In many of these applications, miniaturization creates the need for high-aspect-ratio (i.e., height divided by width) conductive structures. For example, in microneedle applications high-aspect-ratio structures are preferred for their rigidity and consequent ability to penetrate human skin in vivo. In electrical applications, circuit densities continue to increase. As the circuits become smaller, the widths of vias, contacts, and other features, as well as the dielectric materials between them all decrease significantly, whereas the thickness of the dielectric layers remains substantially constant. The result being that many features take on increasingly larger aspect ratios. While conventional structures have been created through well-known techniques such as micromachining of solid conductors, these approaches are not cost-effective and therefore cannot be scaled to larger production.

Electrodeposition has been proposed as an economically viable alternative for making conductive three dimensional structures. Metal electrodeposition is generally well-known and can be achieved by a variety of techniques. A typical method generally comprises depositing a barrier layer over the feature surfaces, depositing a conductive metal seed layer over the barrier layer, and then electroplating a conductive metal over the seed layer to cover the structure. An example of this technique is described in U.S. Pat. No. 7,196,666 by Allen et al., entitled "Surface Micromachined Millimeter-Scale RF System and Method," the disclosure of which is incorporated herein by reference. Although electrodeposition may provide cost savings over micromachining of solid conductive structures, an additional challenge exists in patterning high-aspect-ratio three-dimensional structures due to difficulty in non-planar surface patterning using conventional lithographic approaches. It therefore would be desirable to provide improved methods of efficiently fabricating electrically-conductive structures, particularly high-aspect-ratio structures, in a process that can be scaled for mass-production.

SUMMARY OF THE INVENTION

Methods are provided for fabricating three-dimensional electrically conductive structures. Three-dimensional electrically conductive microstructures are also provided.

In one aspect, a method for fabricating a three-dimensional, electrically conductive structure comprises providing a mold having at least one microdepression which defines a three-dimensional structure; depositing and patterning at least one electrically conductive layer within microdepression of the mold; filling the microdepression of the mold with at least one substrate material; molding the at least one substrate material to form a substrate on top of the at least one electrically conductive layer; and transferring the at least one electrically conductive layer to the substrate to form an electrically conductive structure. The method may further comprise removing the electrically conductive structure from the mold. In one embodiment, the method may further comprise electroplating onto the electrically conductive layer. In still another embodiment, the patterning comprises removing selectively the electrically conductive layer from protruding and/or recessed surfaces of the mold.

In another aspect, a method is provided for fabricating a three-dimensional, electrically conductive structure which includes the steps of providing a mold having at least one microdepression which defines a three-dimensional structure; filling the microdepression of the mold with at least one substrate material; molding the substrate material to form a substrate structure; and depositing at least one electrically conductive layer onto the substrate structure by directional deposition to form an electrically conductive structure.

In still another aspect, a method is provided for fabricating a three-dimensional, electrically conductive structure which includes the steps of providing a mold having at least one microdepression which defines the surface of a three-dimensional structure; filling the microdepression of the mold with at least one substrate material; molding the substrate material to form a substrate structure; depositing a conductive seed layer onto the substrate structure; patterning the conductive seed layer using a laser ablation or other selective ablation technique; and electroplating an electrically conductive layer onto the patterned seed layer to form a electrically conductive structure. In one embodiment, the molding comprises a solvent casting or melt casting technique.

In one embodiment, the mold comprises a photoresist. In one embodiment, the substrate material may be substantially non-electrically conductive. For example, in one embodiment the substrate material comprises a polymer. In one embodiment, the electrically conductive layer comprises nickel, iron, gold, titanium, copper, platinum, palladium, a stainless steel, or an alloy thereof.

In one embodiment, the at least one microdepression of the mold defines a high-aspect ratio three-dimensional structure. In a particular embodiment, the electrically conductive structure has an aspect ratio of greater than about 4:1.

In one embodiment, the conductive seed layer comprises an alloy of titanium and copper. The electroplated electrically conductive layer may comprise, for example, a metal selected from the group consisting of nickel, iron, gold, titanium, copper, platinum, palladium, stainless steels, and alloys thereof. The electroplated electrically conductive layer may include, for example, nickel.

In another aspect, an electrically functional microneedle array is provided. The electrically functional microneedle array may include two or more microneedles extending from a base, wherein each microneedle comprises a high aspect ratio, polymeric three dimensional substrate structure which is coated, at least substantially, by an electrically conductive layer. The two or more microneedles may have an aspect ratio of greater than about 4:1.

In certain embodiments, the substrate structure of the microneedle array comprises a polymer. For example, the polymer may be selected from the group consisting of polymethylmethacrylate, polycarbonate, polystyrene, polyethylene terphthalate, polyethylene, polyvinylchloride, cyclic olefin copolymer, polyurethane, polyamide, polysulfone, polylactide, polyglycolide, poly(lactic-co-glycolic)acid, polyacrylonitrile, copolymers thereof and blends thereof.

In one embodiment, the conductive layer of the microneedle array comprises a metal layer having a thickness of between about 10 and about 50 microns. In one embodiment, the microneedles may be tapered. In one embodiment, the two or more microneedles of the microneedle array are electrically isolated from each other.

In one embodiment, the microneedles of the microneedle array further comprise a coating which includes a biological macromolecule. In certain embodiments, the biological macromolecule comprises DNA, RNA, a protein, or a peptide.

Methods are also provided for making microneedle arrays. In one embodiment, the method includes the steps of providing a mold having at least one microdepression which defines a high-aspect ratio three-dimensional structure; depositing and patterning at least one electrically conductive layer within microdepression of the mold; filling the microdepression of the mold with at least one substrate material; molding the at least one substrate material to form a substrate on top of the at least one electrically conductive layer; and transferring the at least one electrically conductive layer to the substrate, thereby forming a high-aspect ratio, electrically conductive array structure.

In another embodiment, the method includes the steps of providing a mold having at least one microdepression which defines a high-aspect ratio three-dimensional structure; filling the microdepression of the mold with at least one substrate material; molding the substrate material to form a high-aspect ratio substrate structure; and depositing at least one electrically conductive layer onto the high-aspect ratio substrate structure by directional deposition to form a high-aspect ratio, electrically conductive array structure.

In still another embodiment, the method includes the steps of providing a mold having at least one microdepression which defines the surface of a three-dimensional structure; filling the microdepression of the mold with at least one substrate material; molding the substrate material to form a high-aspect ratio substrate structure; depositing a conductive seed layer onto the high-aspect ratio substrate structure; patterning the conductive seed layer using a laser ablation or other selective ablation technique; and electroplating an electrically conductive layer onto the patterned seed layer to form a high-aspect ratio, electrically conductive structure.

DETAILED DESCRIPTION OF THE INVENTION

Methods have been developed for coating conductive metals over various moldable, e.g., polymeric, substrates that allows efficient construction of complex 3-D structures, including high-aspect-ratio structures. Advantageously, once a master mold master has been made, several thousand parts can be molded with little effort. In addition, the cost of the raw material in most cases is negligible because only small material quantities are required for microdevice fabrication. Therefore, parts fabricated by micro molding, even from high-end materials, are suitable for applications requiring low-cost and disposable components. The methods provide conductive, high aspect ratio three-dimensional structures.

In one embodiment, the method includes the depositing and patterning of a metal layer, molding of a substrate, and the fusing of the metal layer to the substrate for structural stability. In another embodiment, the depositing and patterning may occur subsequent to the molding of the substrate by direct metal deposition onto the molded substrate or by deposition and laser patterning of a metal seed layer onto the molded substrate. These methods allow for the fabrication mass-production of high-aspect ratio conductive structures in an economical manner.

I. Three Dimensional Metal Transfers

Figure 1A:
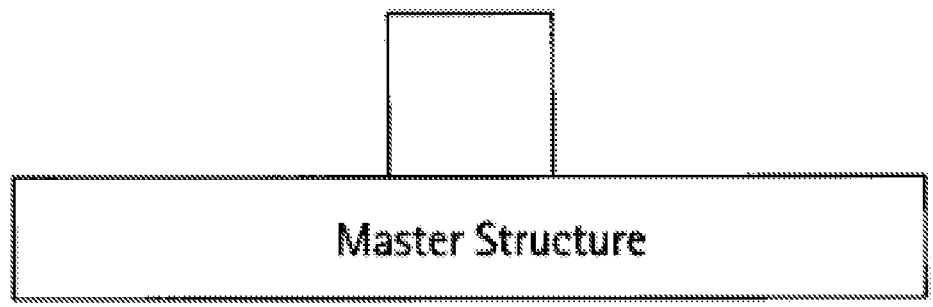
FIG. 1A is a schematic illustration of a micromolding technique including the fabrication of a master structure in accordance with a particular embodiment.
Figure 1B:
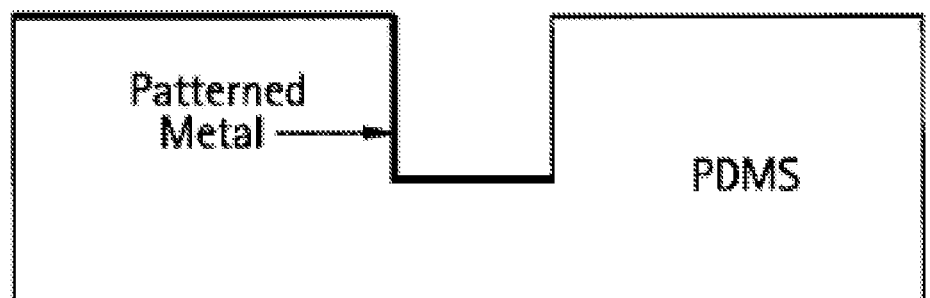
FIG. 1B is a schematic illustration of a micromolding technique including the fabrication of a master mold from the master structure followed by metal deposition and patterning in accordance with a particular embodiment.
Figure 1C:
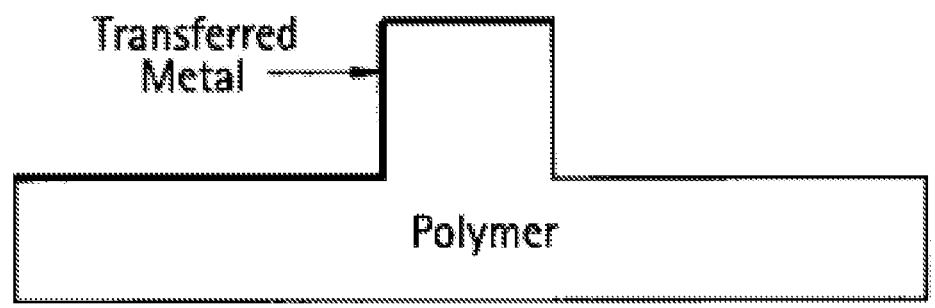
FIG. 1C is a schematic illustration of a micromolding technique including the formation of a three-dimensional metal-patterned polymeric microstructure in accordance with a particular embodiment.

In one embodiment, the method of fabricating a three-dimensional conductive structure comprises a three-dimensional metal transfer molding technique by metallization of a negative form of a master mold (illustrated in FIG. 1). The three-dimensional metal transfer method (illustrated in FIG. 2) comprises (A-B) providing a mold having at least one microdepression defining the surface of a three-dimensional structure; (C-D) depositing and patterning a metal layer within the mold; filling the metal-patterned mold with a substrate; and (E-F) transferring the metal layer to the substrate to obtain a three-dimensional conductive structure. The metal layer may be patterned during metal deposition using a shadow mask or alternatively may be patterned after metal deposition using other methods well known to those of ordinary skill in the art (e.g., selective etching combined with lithography, lift-offs, or the like). The patterning of the metal layer also may be aided by integrated features of the mold, such as protrusions allowing selective removal of portions of the metal by external contact with an adhesive plate. The pre-patterned metal layer subsequently may be transferred from the mold surface to a high surface energy casting material during the molding/demolding process.

Fabrication of a Master Mold

The master mold generally may be prepared from a master structure fabricated using conventional or modified photolithographic techniques. In an exemplary embodiment, illustrated in FIG. 3, the master comprises a rigid SU-8 mold fabricated using inclined UV lithography to form negative concave shapes of various depths (see, e.g., Han et al., Sensors and Actuators A 111: 14-20 (2004); Sato et al., Sensors & Actuators A 111:87-92 (2004); and Yoon et al., Proceedings IEEE MEMS Conf. 227-30 (2003)).

Figure 3A:
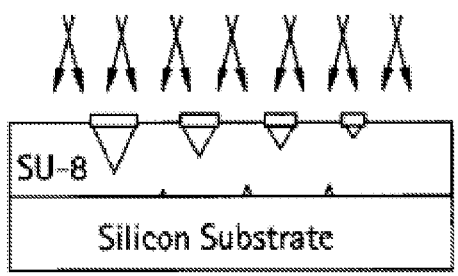
FIGS. 3A-3F are schematic illustrations of a method for fabricating an electrically conductive, three-dimensional structure in accordance with a particular embodiment.
Figure 3B:
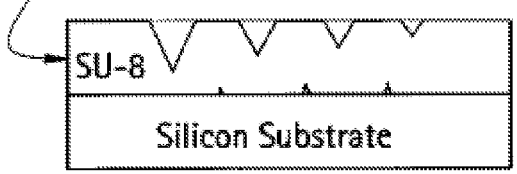

Briefly described, the master structure may be fabricated by depositing a layer of thick, ultraviolet (UV)-sensitive photoresist such as SU-8 epoxy onto a substrate. A lithographic mask may then be used to photoexpose the epoxy in an inclined manner such as that described by Yoon et al., IEEE Journal of Microelectromechanical Systems 15(5): 1121-30 (2006), the disclosure of which is incorporated herein by reference (FIG. 3A). After development of the resist, cavities may be formed in the SU-8 substrate, the size and depth of which depend on the angle of inclination of exposure and the features on the lithographic mask (FIG. 3B).

Figure 3C:
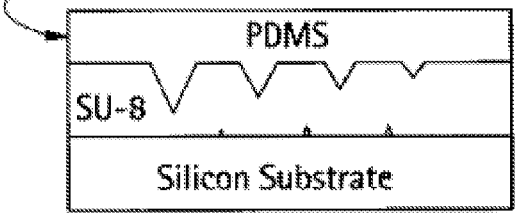
Figure 3D:
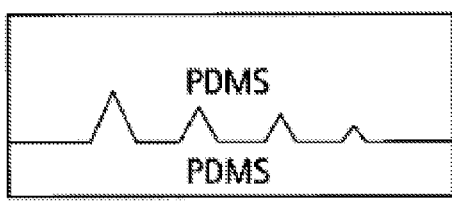

The master structure may be used to produce a mold master from polydimethylsiloxane (PDMS) or other suitable material (such as Ni in the case of electroplating). The PDMS may be molded in the master structure by filling the master structure with the PDMS and curing the PDMS at a temperature of about 80.degree. C. for about 4 hours before removing the master mold from the master structure (FIG. 3C). The mold master then may be used to create a mold comprising a flexible replica of the original rigid master structure using a material such as PDMS due to both its low modulus and low surface energy (FIG. 3D). The resulting mold optionally may be metallized and patterned, as described hereinbelow, prior to molding of a substrate (FIG. 3E) to obtain a three-dimensional structure (FIG. 3F).

Depositing and Patterning of Metal

Figure 2A:
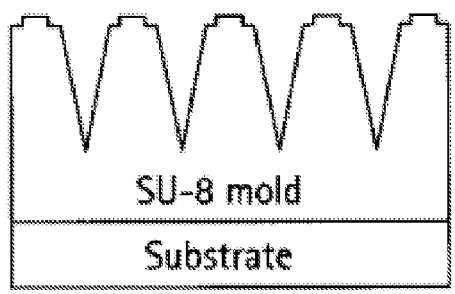
FIGS. 2A-2F are schematic illustrations of a method for fabricating an electrically conductive, three-dimensional structure in accordance with a particular embodiment.
Figure 2B:
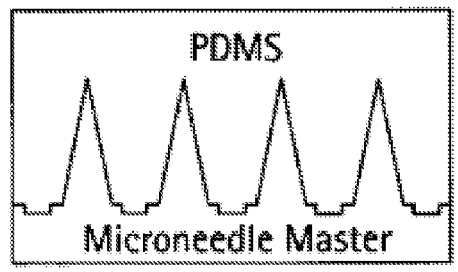
Figure 2C:
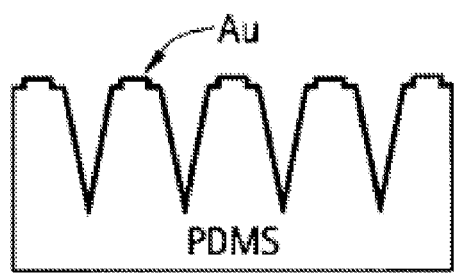
Figure 2D:
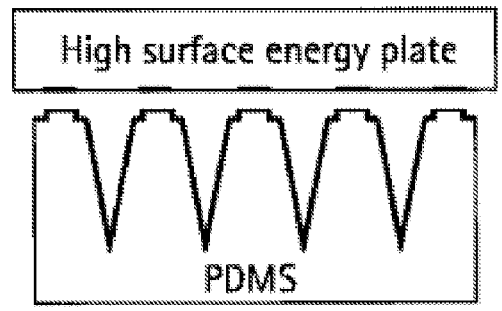
Figure 2E:
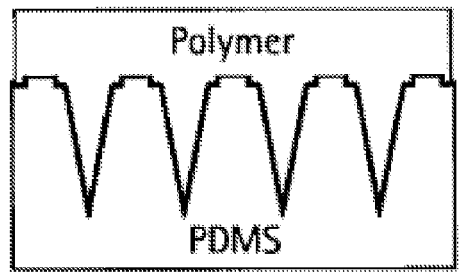
Figure 2F:
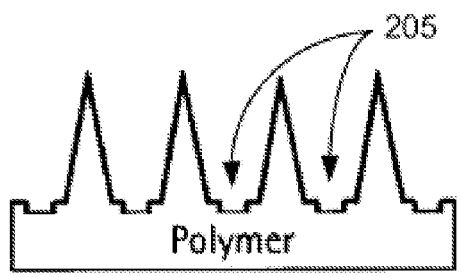

In one embodiment, a metal layer may be deposited to a desired thickness within the mold described hereinabove (FIG. 2C). Essentially any suitable metal deposition technique known in the art may be used. A non-limiting example is a sputter-deposition technique and simultaneous or subsequent patterning of the metal layer. In one embodiment, the patterning may be achieved by utilizing the engineered non-planarity of the mold to realize the metal patterning in a self-aligned fashion, although conventional techniques for patterning also may be used. The mold may be prepared with integral protrusions in the area where metal ultimately may be removed, which is on the uppermost surfaces of the mold, allowing the metal layer to be isolated electrically by contacting the metal layer on the surface of the mold with a substantially flat smooth sticky surface or with a high surface energy plate (FIG. 2D-E). Nonplanar molds and complimentary-shaped or formable nonplanar high surface energy plates also may be used for the electrical isolation. In another embodiment, patterning may be accomplished by using a spin-coated ultra-thin layer of stereo lithography apparatus (SLA) resin or polyurethane (PU) on a smooth substrate. After the polymer is cured, the gold on the top surface of the PDMS is transferred to the polymer surface. As seen in FIG. 2F, the channels 205 extending into the base of the polymer are disposed between the microneedles and correspond to the uppermost protrusions of the mold.

Figure 4A:
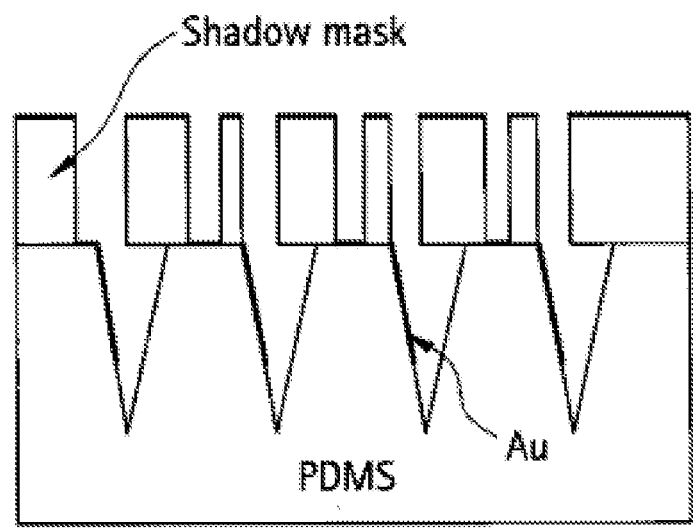
FIGS. 4A-4C are schematic illustrations of a method for depositing and patterning an electrically conductive layer within a mold using a shadow mask approach in accordance with a particular embodiment.
Figure 4B:
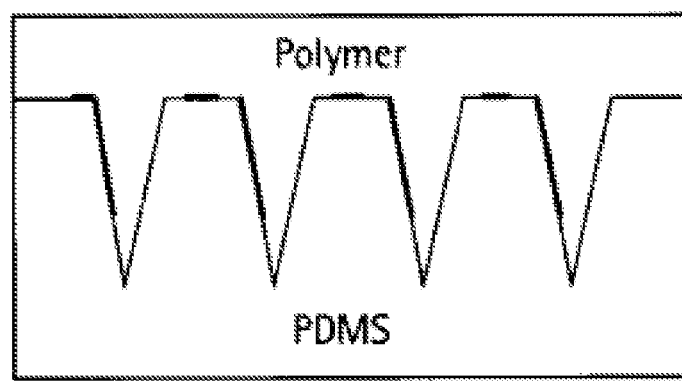
Figure 4C:
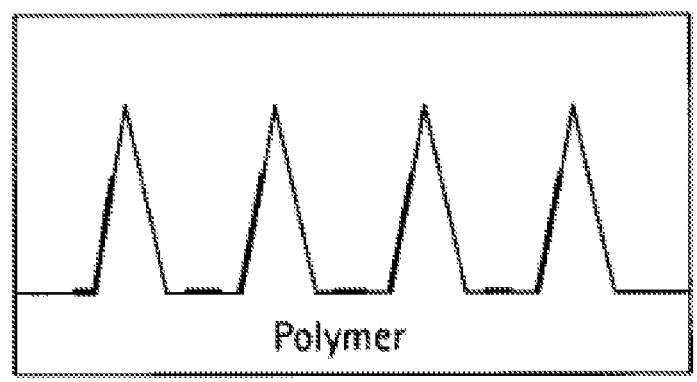

In still another embodiment, the metal layer may be deposited and patterned within the mold using a shadow mask approach (FIG. 4). The shadow mask may be formed from using materials and techniques well known to ordinary skill of the art. In one embodiment, a shadow mask may be aligned with the mold and a patterned metal layer deposited within the mold (FIG. 4A). The substrate then may be cast into the mold and cured (FIG. 4B) using the methods described hereinbelow to obtain a three-dimensional substrate (FIG. 4C).

Final Molding

Figure 3E:
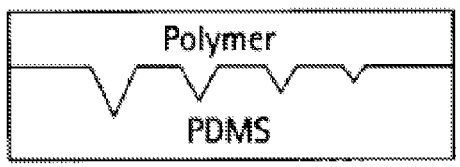
Figure 3F:
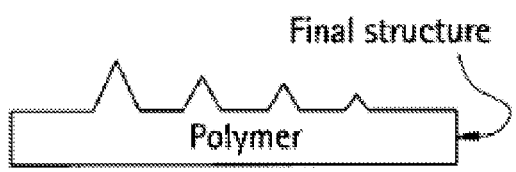

After fabrication of the mold and the optional deposition and patterning of a metal layer, a substrate may be cast into the mold and cured using any suitable technique to obtain a three-dimensional substrate (FIG. 2E & FIG. 3E). For example, the substrate may be cast into the mold using solvent casting, melt casting, or reactive casting and solidified by reactive, thermal, or UV curing.

Upon separation of the three-dimensional substrate from the mold (FIGS. 2F & 3F), the optional patterned metal layer may be transferred to the surface of the three-dimensional structure to provide a conductive three-dimensional structure. Electroplating optionally may be performed subsequent to removal of the three-dimensional substrate from the mold to increase the thickness of the metal layer.

In embodiments wherein the microdepression has an aspect ratio of less than about 3:1, the metal may be conformally deposited within the surface of the mold using a sputtering machine without difficulty. In embodiments wherein the microdepression has an aspect ratio of greater than about 3:1, non-conformal metal coating may occur within deeper portions of the mold and an additional metal deposition step may be required subsequent to the three-dimensional metal transfer molding/demolding step.

II. Molding of Three-Dimensional Structures and Directional Metallization

In another embodiment, the method of fabricating a three-dimensional conductive structure (FIG. 5) comprises (A) providing a mold having at least one microdepression defining the surface of a three-dimensional structure; (B) filing the mold with a substrate to form a three-dimensional substrate; and (C-D) directly depositing and patterning a metal layer onto the three-dimensional substrate.

The mold is prepared from a master structure (FIG. 5A) made from a material chosen for its ability to generate a high aspect ratio structure as well as for its mechanical robustness. A material such as PDMS is then cast against the master structure and cured before removing the mold from the master structure. The resulting mold comprises a negative microdepression of the master structure.

Figure 5A:
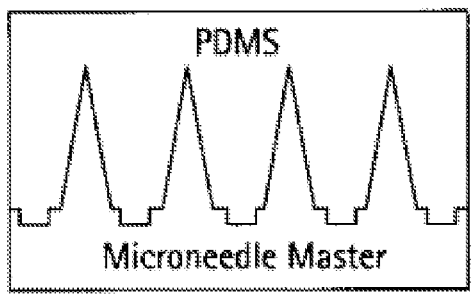
FIGS. 5A-5E are schematic illustrations of a method for fabricating a three-dimensional conductive structure in accordance with a particular embodiment.
Figure 5B:
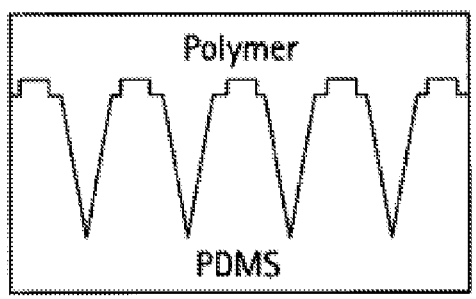

The substrate may be cast into the mold and cured using any suitable technique to obtain the three-dimensional substrate (FIG. 5B). For example, the substrate may be cast into the mold using solvent casting, melt casting, or reactive casting and solidified by reactive, thermal, or UV curing.

Figure 5C:
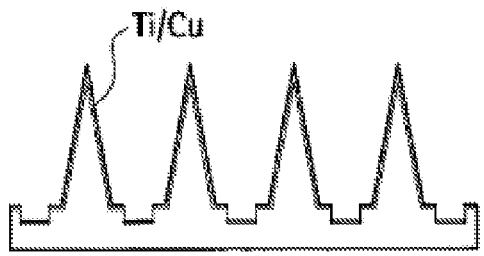
Figure 5D:
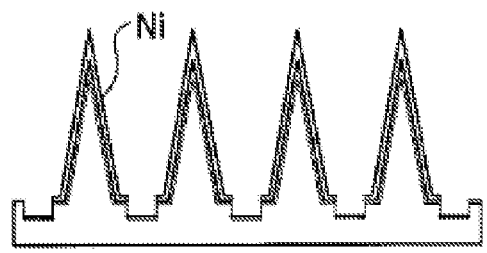
Figure 5E:
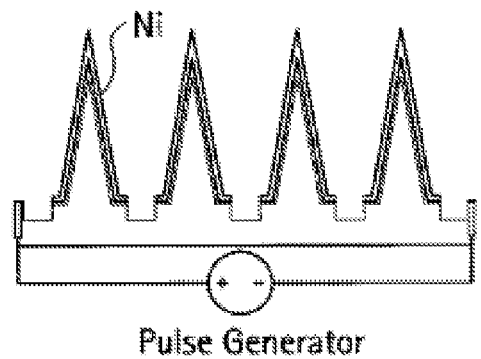

The resulting three-dimensional substrate then may be removed from the mold and a titanium layer and a copper layer with thicknesses of 20 nm and 50 nm, respectively, may be deposited on the three-dimensional substrate using a directional metal deposition tool (FIG. 5C). Non-limiting examples of suitable directional metal deposition tools include a thermal evaporator and an e-beam evaporator. The three-dimensional substrate then may be electrically isolated as desired. The titanium and copper metal layers on the surface of three-dimensional substrate act as a seed layer for subsequent electroplating on the surface of the three-dimensional substrate if desired. For example, a Ni layer with a thickness of 25 μm may be electroplated on the seed layer to strengthen the mechanical rigidity of the three-dimensional substrate.

III. Laser Machining Combined with Subsequent Electrodeposition

In another embodiment of the method of fabricating a three-dimensional conductive structure illustrated in FIG. 6, laser machining may be combined with subsequent electrodeposition of a metal layer. This method permits patterning of an electrical conductive layer on an organic substrate or on an inorganic substrate.

A micromachined master structure may be prepared by spinning a photoresist on a glass substrate bearing a mask pattern, baking, and then exposing the photoresist from the backside to form a three-dimensional micromachined master structure which may be modified using methods such as reactive ion etching (not shown).

Figure 6A:
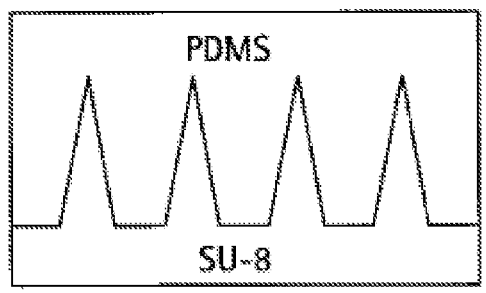
FIGS. 6A-6E are schematic illustrations of a method for fabricating a three-dimensional conductive structure in accordance with a particular embodiment
Figure 6D:
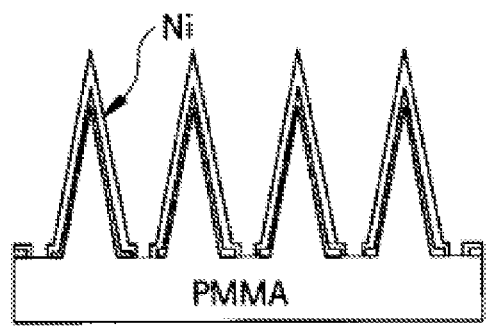
Figure 6B:
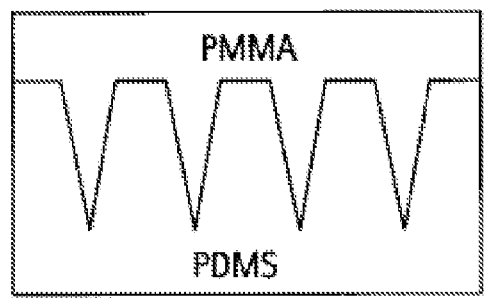
Figure 6E:
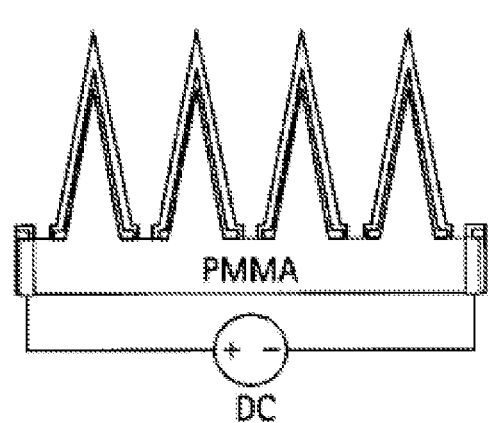
Figure 6C:
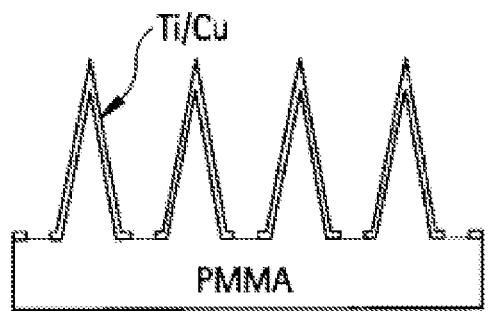

A material such as PDMS may be cast onto the micromachined master structure to form a mold (FIG. 6A) into which a substrate may be cast and cured to obtain a three-dimensional substrate (FIG. 6B). A titanium and copper seed layer with thicknesses of 20 nm and 50 nm, respectively, may be deposited on the three-dimensional substrate by DC sputtering and patterned by excimer laser ablation (FIG. 6C). A metal layer may be electroplated on the patterned seed layer to enhance structural rigidity (FIG. 6D) and an electrical may be made between the three-dimensional substrate and external electronics using a backside connection (FIG. 6E).

IV. Conductive Three-Dimensional Structures and Uses

A wide variety of electrically conductive three dimensional structures, e.g., microstructures, can be made with the methods described herein. In a preferred embodiment, the structures are high-aspect ratio structures. For example, the methods may be used to make a single high-aspect ratio three dimensional structure or to make multiple high-aspect ratio three dimensional structures, such as in an array of two or more of the conductive structures. As used herein, the term "high aspect ratio" means that the metal coated three dimensional structure has an aspect ratio (height:width) greater than about 3:1. In a preferred embodiment, the aspect ratio is 4:1 or greater (e.g., 5:1, 8:1, or 15:1). In one embodiment, the aspect ratio is between 4:1 and 10:1. Other lengths, widths, and aspect ratios are envisioned.

In various embodiments, the 3D structure may have a length of between about 50 μm and about 5000 μm, preferably between about 100 μm and about 1500 μm, and more preferably between about 200 μm and about 1000 μm. In one embodiment, the length of the structure is about 750 μm. In various embodiments, the base portion of the structure has a width or cross-sectional dimension between about 20 μm and about 500 μm, preferably between about 50 μm and about 350 μm, more preferably between about 100 μm and 250 μm.

In a preferred embodiment, an electrically functional microneedle array is provided. In one embodiment, the microneedle array includes two or more microneedles extending from a base, wherein each microneedle comprises a high aspect ratio, non-conducting three dimensional substrate structure which is coated by a conductive metal layer. The metal coating may cover all or some lesser majority portion of the microneedles. In one embodiment, the coating may not be continuous between some or all of the microneedles, such that two or more microneedles are electrically isolated from each other.

The microneedles may have a straight or tapered shaft. In one embodiment, the diameter of the microneedle is greatest at the base end of the microneedle and tapers to a point at the end distal the base. The microneedles may also have a shaft that includes both a straight (i.e., untapered) portion and a tapered portion. The microneedles may be formed with shafts that have a lateral cross-sectional shape that is circular or non-circular. That is, the lateral periphery may be round or have a polygon shape. In one embodiment, the microneedle device includes a substantially planar base from which one or more microneedles extend, typically in a direction normal (i.e., perpendicular or 'out-of-plane') to the base. The tip portion of the microneedles may be symmetrical or asymmetrical about the longitudinal axis of the shaft. The tips may be beveled, tapered, squared-off or rounded, depending upon the particular application.

The substrate structure may comprise a polymer, ceramic, or other moldable electrical insulator material. This substructure may be made from a variety of materials, including thermoplastic polymers, thermoset polymers, biodegradable polymers, precursor polymers to carbons and ceramics, polymer composites, polymer blends, and interpenetrating polymer networks, among others. Representative examples of suitable polymeric substrate materials include poly(lactide)s, poly(glycolide)s, poly(lactide-co-glycolide)s, poly(lactic acid)s, poly(glycolic acid)s, poly(lactic acid-co-glycolic acid)s, polyanhydrides, polyorthoesters, polyetheresters, polyesters (e.g., polyethylene terephthalate and polycarbonate), polycaprolactones, polyesteramides, poly(butyric acid), poly(valeric acid), polyurethanes, polyacrylates (e.g., polymethylmethacrylate), polymers of ethylene-vinyl acetates and other acyl substituted cellulose acetates, polyamides, polyimides, polystyrenes, polysulfones, polyvinyl chloride, polyvinyl fluoride, poly(vinyl imidazole), chlorosulphonate polyolefins, polyethylene oxide, epoxies, blends and copolymers thereof.

In one embodiment, the high-aspect ratio three dimensional structures are in the form of a microneedle array for biomedical applications, such as for insertion into or through a biological tissue. The microneedle may be tailored to provide, among other things, the mechanical strength to remain intact while being inserted into the skin, while remaining in place during its functional period, and while being removed.

The microneedle optionally may include a releasable coating material on the surface of the microneedles. In one embodiment, the coating may include a plurality of discrete microparticles or other particles. The coating may consist only of these particles, packed together to form a coating once a solvent of the coating liquid has been volatilized. Alternatively, these particles may be dispersed within a continuous matrix material. Examples of the particles or microparticles that may form part or all of the coating include solid or gel-like organic or inorganic compounds in a non-dissolving solvent.

In one embodiment, the microneedle array includes a coating which comprises a biological macromolecule, such as a pharmaceutical macromolecule. Non-limiting examples of possible biological macromolecules include therapeutic or prophylactic proteins, peptides, genetic material such as plasmid DNA and oligonucleotides, vaccines, cells, virus particles, prions, or combinations thereof. Coated microneedles are also particularly attractive for vaccine delivery to the skin, because antigens can be targeted to epidermal Langerhans cells and dermal dendritic cells for a more potent immune response. In another embodiment, the coating comprises nanoparticles for delivery into the skin of a patient in need thereof. In one case, drug molecules are incorporated into a microparticle or nanoparticles form. In one embodiment, the coating is applied as taught in PCT Application Publication No. WO 2006/138719 by Gill & Prausnitz.

In accordance with another aspect of the invention, an electrode assembly is provided that includes an array of the electrically functional, high-aspect ratio three-dimensional structures made as described herein. In one embodiment, the electrode assembly is part of an electroporation apparatus for the delivery of molecules into biological cells, in vitro or in vivo. In one embodiment, the apparatus includes the electrode assembly, a holder for the electrode assembly, and a waveform generator, which may provide pulse waveforms. The array of electrodes of the electrode assembly may be electrically connected to the waveform generator through electrically conductive pathways. The electrodes desirably are coated with a biological macromolecule or other active agent useful in a medical therapy or prophylaxis. For example, the electrode arrays having a high-aspect ratio three-dimensional structure as described herein may be adapted for use with the methods and apparatus described in U.S. Pat. No. 6,713,291 to King et al. and in U.S. Patent Application Publication No. 2004/0203124 to King et al.

In still other aspects of the present invention, electrically functional, high-aspect ratio three-dimensional structures made as described herein may be used in metal pillar arrays for solid fuel combustion, electromagnetically radiating antenna arrays, and other micro-electronics.

The present invention may be further understood with reference to the following non-limiting examples.

Example 1

Microneedle Fabrication

A microneedle device including a 16.times.16 array of electrically active microneedles was fabricated with adjacent microneedle rows electrically isolated. The height of the microneedles was 400 µm, bottom diameter was 100 µm, and pitch between microneedles was 250 µm.

The microneedle device was fabricated by mold replication from a micromachined master. To fabricate the master structure, SU-8 was spun on a glass substrate bearing an array mask pattern, baked, and then exposed from the backside to form the tapered needle structure. The microneedles were sharpened by RIE etching. A PDMS (polydimethylsiloxane) mold was copied from the master (FIG. 6A) and a PMMA (polymethylmethacrylate) microneedle array (FIG. 6B) was formed by solvent-casting and then released from the mold.

The PMMA was prepared from a PMMA powder ($M_W$=75, 000, Scientific Polymer Products Inc., USA) dissolved in ethyl 1(—)-lactate (Acros Organics, USA). Due in part to the reduction of viscosity achieved with the polymer solution, void-free molding and subsequent microneedle fabrication were successful.

To achieve electrical functionality, a Ti/Cu seed layer (300 Å/3000 Å) was deposited on the PMMA array using DC sputtering and patterned by excimer laser ablation to electrically isolate adjacent microneedle rows with a 100 µm gap (FIG. 6C). A 25 µm thick Ni layer was electroplated on the patterned seed layer at room temperature with stifling to enhance structural rigidity (FIG. 6D).

For electrical connection between the microneedle array and external electroporation electronics, a backside connection was formed by $CO_2$ laser etching of the backside of the PMMA substrate to form a via (FIG. 6E). Copper wire was passed through the via and connected to the underside of the metallization using silver paste followed by an epoxy mechanical connection.

Example 2

Mechanical Strength of Microneedle Electrodes

The microneedle electrodes prepared in Example 1 were analyzed to determine whether their mechanical properties were sufficient for insertion into the skin. The yield stress of the microneedle array to an axial load was determined by using a force-displacement testing station (Tricor Systems, USA). The microneedle array was attached to the specimen holder of the force-displacement test station and then pressed against a rigid metal surface at a rate of 1.1 mm/s. Stress versus strain curves were then extracted from the measured force vs. displacement data. The failure force of the microneedle array also was determined from the force versus displacement data by correlation to a sudden drop in measured force, which represents the failure point. The microneedle array was examined under microscope before and after the test to determine the mode of failure.

For the solvent-cast PMMA microneedle array, the average failure force per microneedle was 0.018 N. The addition of 25 µm thick Ni significantly improved the mechanical strength of the microneedle array, providing an average failure force 0.7 N. Previous tests have shown that microneedles of this geometry insert into skin with a force of 0.01 N, indicating that Ni-coated needles should be sufficiently robust for transdermal applications.

To examine the skin penetration ability of the microneedle array, several insertion tests were performed on human subjects using either non-coated (polymer-only) PMMA microneedles or nickel-coated PMMA microneedles having various nickel thicknesses. After removal of the microneedles, the skin was stained with blue dye and observed by microscopy to determine whether the microneedle electrodes pierced into the skin. The microneedle electrodes subsequently examine microscopically to evaluate the condition of the microneedle electrode tips.

The polymer-only array was unable to penetrate through human skin. The PMMA microneedle array with a 10 µm thick electrodeposited Ni layer was sufficiently strong to penetrate through human skin; however, the tips of these microneedle electrodes bent after several successive insertions. PMMA microneedle arrays with a 25 µm thick electrodeposited Ni layer were sufficiently strong to penetrate through human skin without damaging the tips of the microneedle electrode, even after multiple insertions.

Example 3

Electroporation of Microneedle Array

Figure 7:
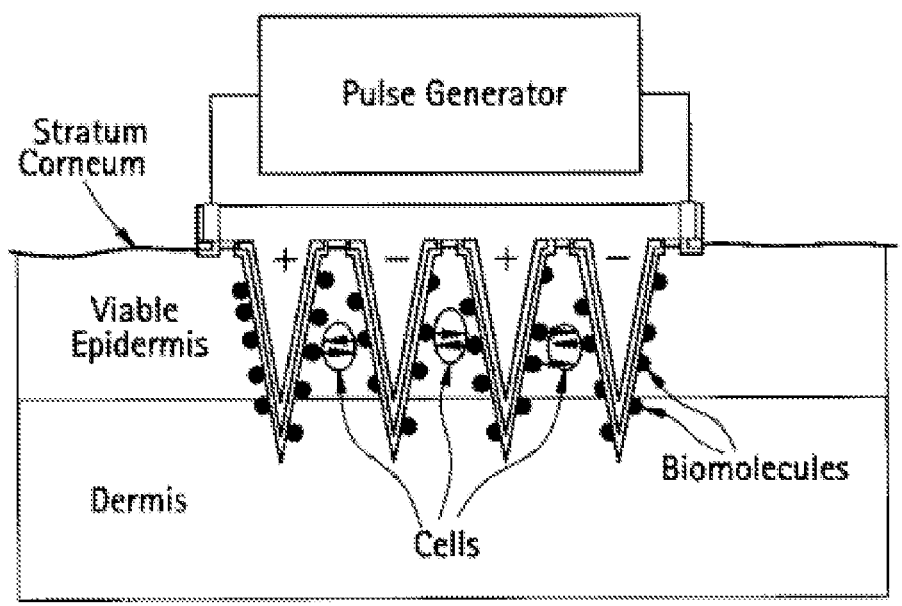
FIG. 7 is a schematic illustration of electroporation using a microneedle array connected to electrical circuitry in accordance with a particular embodiment.

To test the electroporation ability of the microneedle array, an in vitro red blood cell (RBC) lysis assay was performed to quantify the electroporation effect. Approximately 20 ml of bovine blood in alsevers anticoagulant (Rockland Inc., USA) was measured into a 50 ml polypropylene centrifuge tube. Phosphate buffered saline (PBS) was added to the tube which was then centrifuged at 236 G for 10 minutes. The supernatant was discarded and three 20 ml PBS washes were conducted, the supernatant was discarded, and a resultant RBC pellet was formed. The microneedle array was affixed to a surface with the microneedles projecting upward. The array was connected to electrical circuitry to provide a controlled electroporation pulse with an exponential decay waveform (FIG. 7). For each electroporation experiment, 25 µl of concentrated RBC pellet was pipetted onto the microneedle array. Three different peak voltage levels of 53, 108 and 173 volts each were applied each using (i) 1 pulse with an exponential decay time constant τ=0.5 ms, (ii) 3 pulses with τ=0.5 ms and (iii) 1 pulse with τ=1 ms.

After pulse application, the 25 µl RBC suspension was pipetted off into a centrifuge tube. An additional 1 ml PBS was added to the tube and centrifuged at 735 G for 5 minutes. After centrifugation, 700 µl of the supernatant was collected for quantifying the amount of hemoglobin using absorption spectroscopy. A negative control was prepared without application of the electrical pulse while a positive control was prepared by adding 1 ml deionized water to 25 µl of RBC pellet to cause osmotic rupture of all RBCs.

Hemoglobin in the samples was quantified using absorption spectroscopy at 575 nm absorption wavelength. The amount of hemoglobin in the samples was calculated as a percentage of positive control, which was reported as RBC lysis (%). The results were normalized by multiplying by a factor of 3.9 to account for the differences in the volume of RBC applied onto the array (25 µl) and the effective volume available for electroporation (approximately 6.4 µl).

Figure 8:
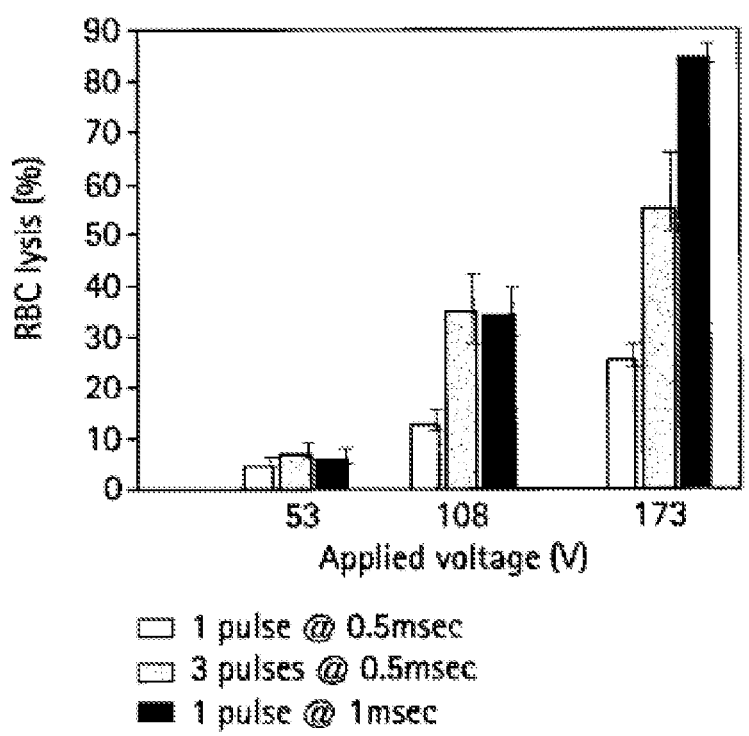
FIG. 8 is a graph illustrating the hemoglobin released from red blood cells (as a percentage of red blood cell lysis) after electroporation with a microneedle array.

The results from RBC electroporation via microneedles shown in FIG. 8 illustrate the percentage of RBC lysis versus the voltage applied. There was a statistically significant increase in electroporation of RBCs as the applied voltage increased ($p<0.0001$). Electroporation of as high as 84% was achieved at 173 V and 1 pulse with 1 ms pulse duration. A separate ANOVA analysis performed to identify the effect of pulse length and pulse duration on electroporation indicates that RBC lysis increased with both pulse length and pulse duration ($p<0.0001$).

Example 4

Electronic Field Simulation

A 3-D finite element (FE) model was created using FEM-LAB 3.1 to examine the electric field distribution around the microneedle array. To mimic the real device, the model consisted of 16 microneedles with the same geometrical parameters as the microneedle array. The 4 microneedles located at the center of the model were analyzed.

Figure 9:
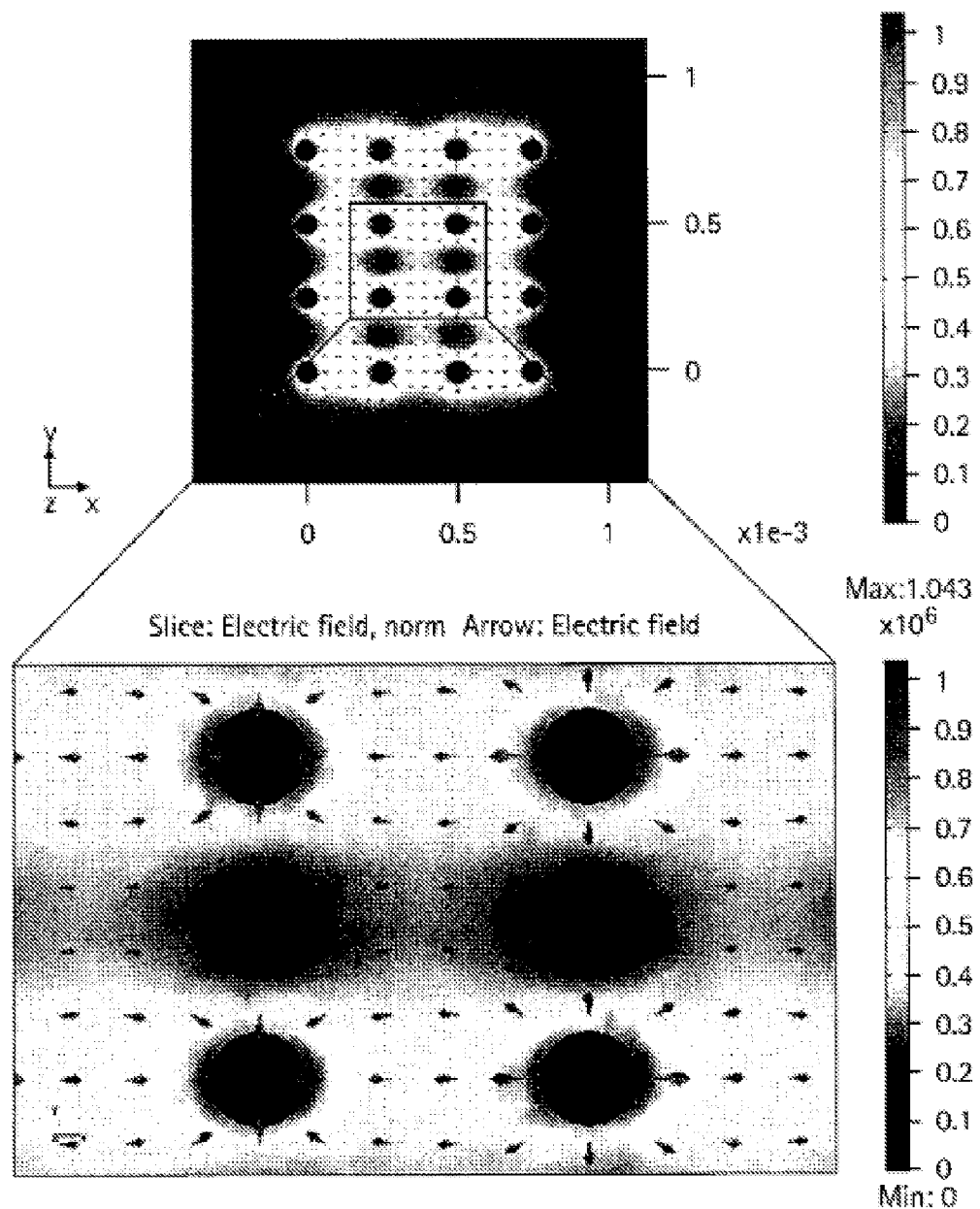
FIG. 9 is a schematic illustration of the electric field distribution of a microneedle array created by a three-dimensional finite element (FE) model.

FIG. 9 shows the top view the of electric field distribution at a height of 100 .mu.m, approximately the height where the viable epidermis is located. The simulation results demonstrated that with 100 V applied between two adjacent rows, a maximum field strength of approximately 10 kV/cm was generated. This field strength may be too high for electroporation for delivering biomolecules; however, it is suitable for cell lysis. At the middle of two adjacent rows, the field strength was about 4 kV/cm.

These results indicate that the field strengths scale with the applied voltage and therefore can be optimized for specific applications. However, implicit in this design are "dead regions" where electroporation cannot occur between two microneedles with the same electric potential. One may optimize the geometry of the microneedle array through FE analysis in order to reduce the effective areas of both the "highly active" and "dead" regions, thereby providing both high rates of biomolecule delivery via electroporation and high survival rates of electroporated cells.

Publications cited herein and the materials for which they are cited are specifically incorporated by reference. Modifications and variations of the methods and devices described herein will be obvious to those skilled in the art from the foregoing detailed description. Such modifications and variations are intended to come within the scope of the appended claims.

The invention claimed is:

1. A method for fabricating a three-dimensional, electrically conductive structure comprising:
   providing a mold having at least one microdepression which defines a three-dimensional structure;
   depositing and patterning at least one electrically conductive layer within the microdepression of the mold;
   filling the microdepression of the mold with at least one substantially electrically non-conductive substrate material;
   molding the at least one substrate material to form a substrate on top of the at least one electrically conductive layer while the at least one non-conductive substrate material abuts an outer surface of the at least one electrically conductive layer opposite the mold; and
   transferring the at least one electrically conductive layer to the substrate, thereby forming an electrically conductive structure.

2. The method of claim 1, further comprising removing the electrically conductive structure from the mold.

3. The method of claim 1, further comprising electroplating onto the electrically conductive layer.

4. The method of claim 1, wherein the mold comprises a photoresist or polydimethylysiloxane.

5. The method of claim 1, wherein the substrate material comprises a polymer.

6. The method of claim 1, wherein the electrically conductive layer comprises nickel, iron, gold, titanium, copper, platinum, palladium, a stainless steel, or an alloy thereof.

7. The method of claim 1, wherein the patterning comprises selectively removing at least a portion of the electrically conductive layer from an upper surface of at least one protrusion of the mold.

8. The method of claim 1, wherein the patterning comprises depositing the electrically conductive layer onto protruding and/or recessed surfaces of the mold through a shadow mask or a stencil mask.

9. The method of claim 1, wherein the at least one microdepression defines a high-aspect ratio three-dimensional structure.

10. The method of claim 1, wherein the mold further comprises at least one upper protrusion that defines a channel within the three-dimensional structure.

11. A method for fabricating a three-dimensional, electrically conductive structure comprising:
    providing a mold having at least one microdepression which defines a three-dimensional structure and at least one upper protrusion which defines a channel within the three-dimensional structure;
    depositing and patterning at least one electrically conductive layer within the microdepression of the mold, the patterning comprising selectively removing at least a portion of the electrically conductive layer from an upper surface of the upper protrusion of the mold;
    filling the microdepression of the mold with at least one substrate material; and
    molding the substrate material to form a substrate structure.

12. The method of claim 11, further comprising electroplating onto the electrically conductive layer.

13. The method of claim 11, wherein the mold comprises a photoresist or polydimethylysiloxane.

14. The method of claim 11, wherein the substrate comprises a polymer.

15. The method of claim 11, wherein the electrically conductive layer comprises nickel, iron, gold, titanium, copper, platinum, palladium, a stainless steel, or an alloy thereof.

16. The method of claim 11, wherein the at least one microdepression defines a high-aspect ratio three-dimensional structure.

17. The method of claim 11, wherein the depositing of at least one electrically conductive layer is achieved using a shadow mask.

18. A method for fabricating a three-dimensional, electrically conductive structure comprising:
    providing a mold having at least one microdepression which defines a three-dimensional structure;
    filling the microdepression of the mold with at least one substrate material;
    molding the substrate material to form a substrate structure;
    depositing a conductive seed layer onto the substrate structure;
    patterning the conductive seed layer using a selective ablation technique, wherein the patterning comprises selectively removing at least a portion of the conductive seed layer from a lower surface of at least one protrusion of substrate structure; and
    electroplating an electrically conductive layer onto the patterned seed layer to form an electrically conductive structure.

19. The method of claim 18, wherein the mold comprises a photoresist or polydimethylsiloxane.

20. The method of claim 18, wherein the molding comprises a solvent casting or melt casting technique.

21. The method of claim 18, wherein the substrate material comprises a polymer.

22. The method of claim 18, wherein the conductive seed layer comprises an alloy of titanium and copper.

23. The method of claim 18, wherein the electroplated electrically conductive layer comprises a metal selected from the group consisting of nickel, iron, gold, titanium, copper, platinum, palladium, stainless steels, and alloys thereof.

24. The method of claim 18, wherein the at least one microdepression defines a high-aspect ratio three-dimensional structure.

25. The method of claim 18, wherein the mold further comprises at least one upper protrusion that defines a channel within the three-dimensional structure.

26. The method of claim 1, wherein the electrically conductive structure has an aspect ratio of greater than about 4:1.

27. The method of claim 11, wherein the electrically conductive structure has an aspect ratio of greater than about 4:1.

28. The method of claim 18, wherein the electrically conductive structure has an aspect ratio of greater than about 4:1.

29. The method of claim 11, wherein molding the substrate material to form the substrate structure comprises positioning the at least one substrate material to abut an outer surface of the at least one electrically conductive layer opposite the mold.

30. The method of claim 11, wherein the substrate material is substantially electrically non-conductive.

31. The method of claim 18, wherein the substrate material is substantially electrically non-conductive.

* * * * *